United States Patent [19]

Cosentino

[11] Patent Number: 4,496,350
[45] Date of Patent: Jan. 29, 1985

[54] BLOOD ACCESS DEVICE

[75] Inventor: Louis C. Cosentino, Wayzata, Minn.

[73] Assignee: Renal Systems, Inc., Minneapolis, Minn.

[21] Appl. No.: 507,197

[22] Filed: Jun. 23, 1983

Related U.S. Application Data

[63] Continuation of Ser. No. 261,719, May 8, 1981, abandoned, which is a continuation of Ser. No. 138,579, Apr. 8, 1980, abandoned.

[51] Int. Cl.³ .............................................. A61M 5/00
[52] U.S. Cl. ........................................ 604/175; 604/4
[58] Field of Search ..................... 604/4, 8, 9, 175, 86, 604/905, 280; 128/1 R

[56]  References Cited

U.S. PATENT DOCUMENTS

| | | | |
|---|---|---|---|
| 3,630,198 | 12/1971 | Henkin ................................ | 604/280 |
| 3,765,032 | 10/1973 | Palma ................................. | 604/175 |
| 3,898,988 | 8/1975 | Morgan ................................ | 604/86 |
| 4,015,601 | 4/1977 | Bokros et al. ........................ | 604/175 |
| 4,108,173 | 8/1978 | Slivenko et al. ...................... | 604/175 |
| 4,164,221 | 8/1979 | Bentley et al. ....................... | 604/175 |
| 4,190,048 | 2/1980 | Sampson .............................. | 604/175 |
| 4,350,157 | 9/1982 | Hoffa ................................. | 604/175 |
| 4,405,320 | 9/1983 | Cracauer et al. ..................... | 604/175 |
| 4,421,507 | 12/1983 | Bokros ................................ | 604/175 |

Primary Examiner—C. Fred Rosenbaum
Assistant Examiner—Michelle N. Lester
Attorney, Agent, or Firm—Schroeder, Siegfried, Vidas & Arrett

[57]  ABSTRACT

A T-shaped blood access device which is adapted for implantation into a patient and which has its stem portion extending outwardly above the skin of the patient. An elastomeric septum is positioned in sealing relationship in the stem adjacent the junction with the main conduit portion. The septum is compressed between a support extension within the device stem and a pressure plate above the septum. The septum is provided with pre-formed openings therethrough to provide a resealable pathway for a needle pair. The septum may have a concave edge to facilitate sealing along the interior device edges and to accommodate laterally displaced septum material during needle insertion. A needle assembly which includes a pair of round ended needles with side openings is preferably used with the T-shaped device. The needle assembly may include a pair of spring loaded sleeve members which normally surround the needles so as to cover the needle side openings during insertion through the septum but which expose the openings as the needles are pushed further downward into the blood stream. A cavity above the septum and a cooperating flanged snap-on cap are provided for keeping the assembly sterile between uses by use of a sterilizing fluid. The arms of the T may be connected directly to the circulatory system or by means of an intermediate polymeric vascular graft.

21 Claims, 13 Drawing Figures

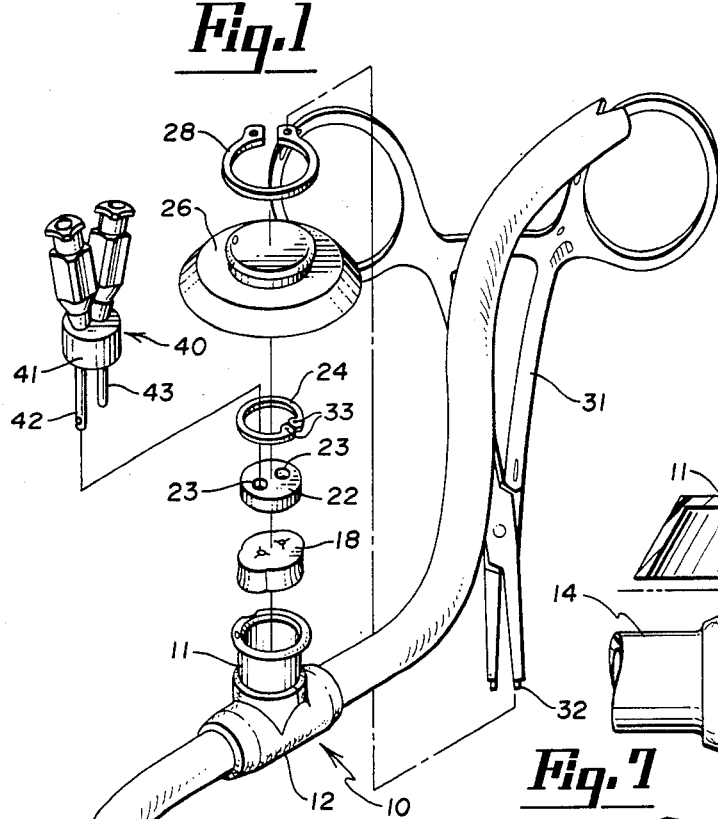
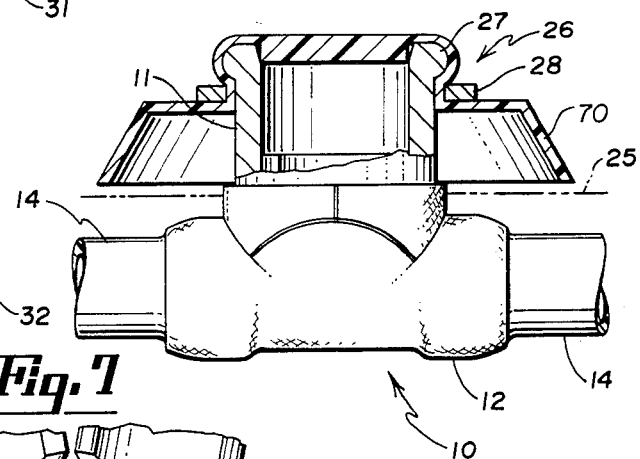
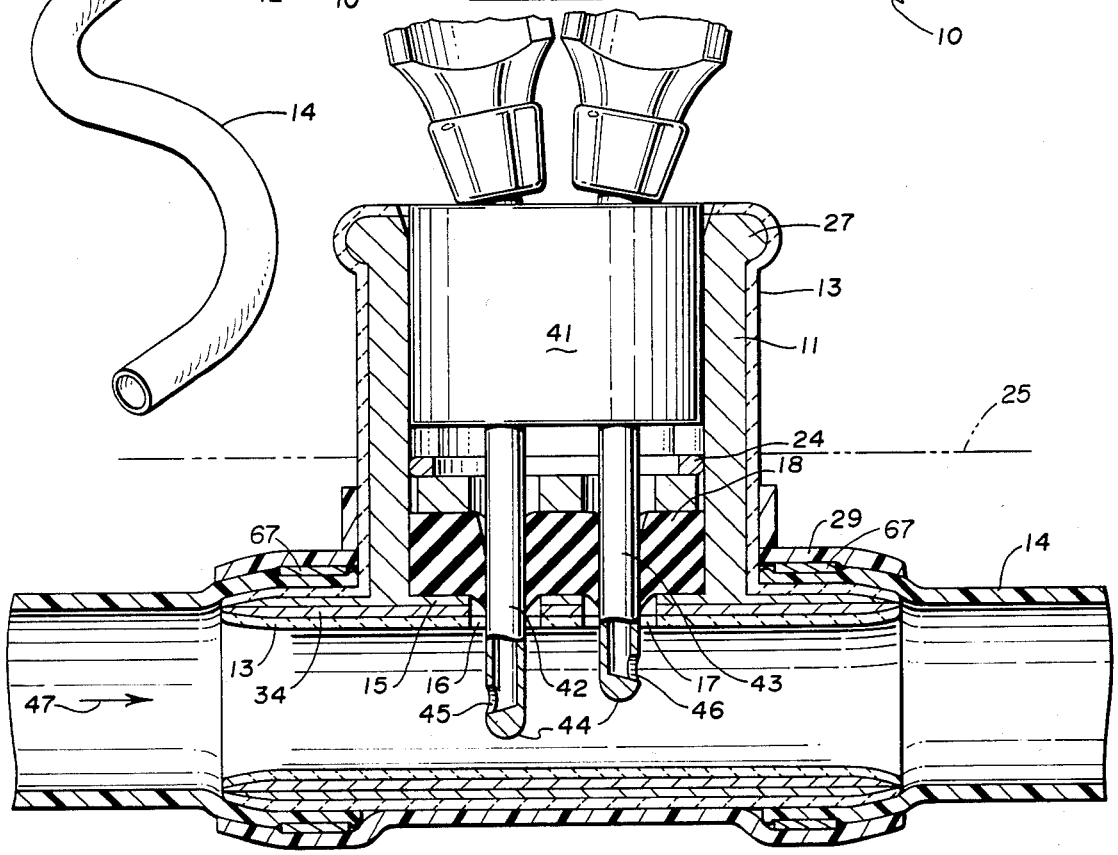

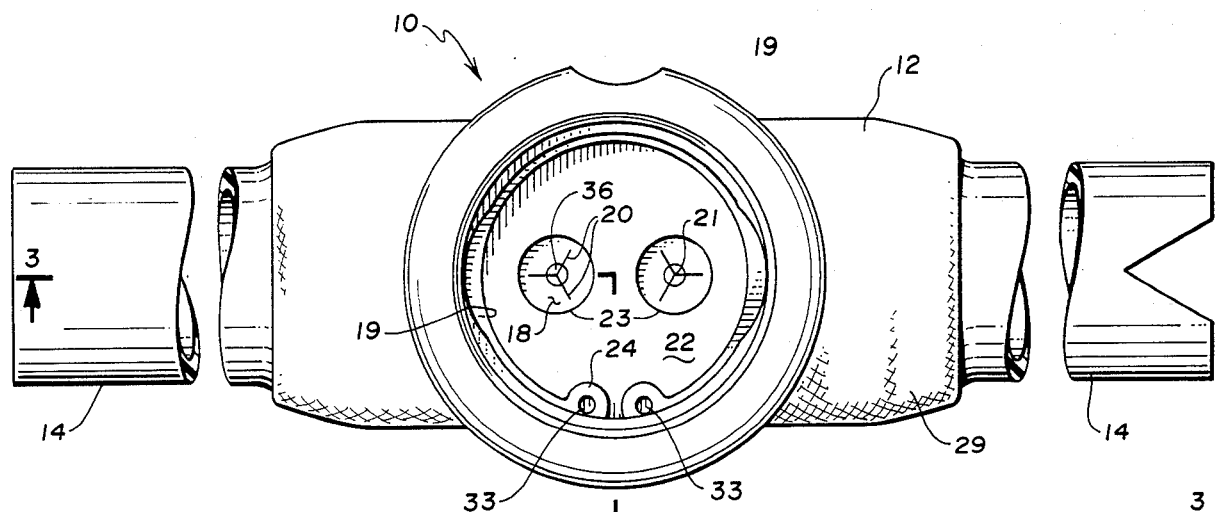
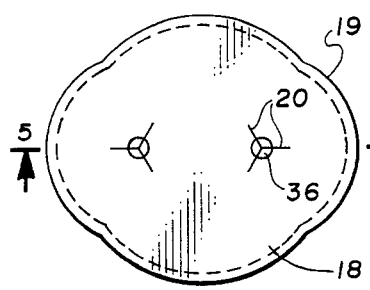
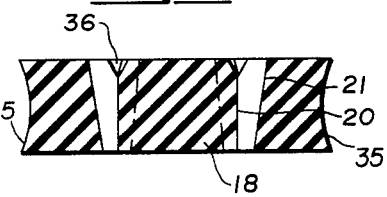
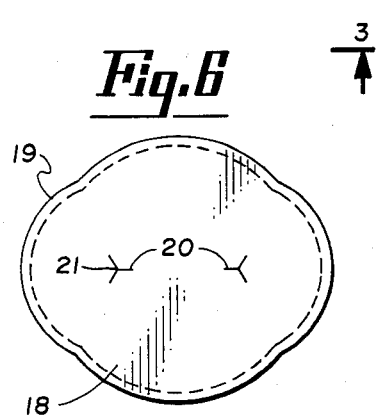
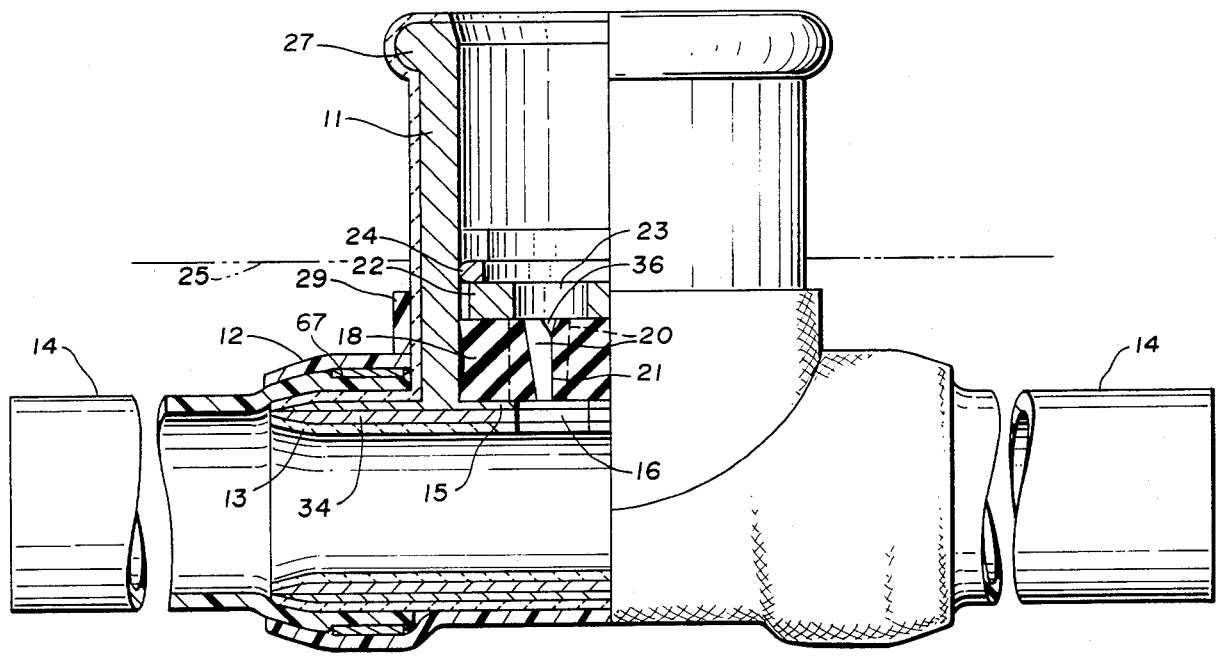

BLOOD ACCESS DEVICE

DESCRIPTION

Background of Invention

The present application is a continuation of Ser. No. 261,719 filed May 8, 1981 and now abandoned, which in turn is a continuation of Ser. No. 138,579 filed Apr. 8, 1980 and now abandoned.

The present invention is directed to an implantable device providing access to the blood circulatory system. While applications for the device can be for a variety of purposes, it is anticipated that principal uses will be in the field of hemodialysis of chronic uremic patients, as access for blood sampling and for treatment of diseases such as diabetes and for forms of chemotherapy and hyperalimentation.

Various approaches to implanted blood access devices are known, however, none of these have been entirely satisfactory. Shunt techniques have problems of infection, clotting and erosion. The arteriovenous fistula has some advantages over shunts but there is a need for recurring needle puncture and there still are infection problems as well as other disadvantages.

It is also known to provide implanted blood access devices wherein access to the circulatory system is accomplished by means of a percutaneous spigot valve.

In accordance with the present invention, an implantable generally tubular T-shaped structure is provided in which the stem of the T is constructed and arranged to cooperate with a novel needle structure that penetrates the seal means at the junction of the stem of the T with the balance of the T structure. By reason of the structure of the invention, the interior stem portion of the T can be rinsed clean and sterilized between each use without elaborate procedures, thus minimizing the likelihood of infection as a result of access to the circulatory system.

It is an object of the invention to provide an implantable blood access device which may be semi-permanently installed into the circulatory system and used repeatedly without need to use expensive surgical procedures for cleaning and sterilizing between uses.

It is a further object of the invention to provide such a device wherein by modification of the cooperating structure, the implanted portion of the device can be readily used with one, two or more needles to gain access to the body's circulatory system.

It is a further object of the invention to provide an implantable blood access device which has a low profile body external portion so as to minimize the possible catching of clothing and the like on the external portion.

A still further object of the invention is to provide a new needle assembly especially adapted to penetrate a septum with sleeve members overlying side opening needles during the penetration while exposing the openings for injection or withdrawal of material once the needle is exposed to the interior of the blood conduit.

These and other objects are accomplished by the construction in accordance with the following description wherein:

BRIEF DESCRIPTION OF DRAWINGS

FIG. 1 is an exploded pictorial view of a device in accordance with the invention including the implantable portion, a two needle cooperating member and a modified forceps for use in assembly and disassembly of the implanted septum assembly;

FIG. 2 is a plan top view of the implantable T-shaped assembly;

FIG. 3 is a side elevational view partly in section as taken along the lines 3—3 of FIG. 2;

FIG. 4 is a plan view of the septum;

FIG. 5 is a section view along lines 5—5 of FIG. 4;

FIG. 6 is a plan view of the bottom or interior facing side of the septum;

FIG. 7 is a sectional view of a device in accordance with the invention with the cooperating needle assembly in operative engagement with the implantable portion;

FIG. 8 is a side elevational view partly in section of the T-shaped implantable structure and cover assembly;

Referring to the drawings (where like parts in the several views will have the same numerical designation) there will be seen in FIG. 1 a device in accordance with the invention which includes a T-shaped unitary tubular body generally designated 10 having a stem portion 11 and a straight tube portion 12. Body 10 is formed of a unitary body of a biologically compatible material such as titanium. It is highly advantageous that body 10 be of a unitary construction to eliminate extraneous cavities at points of assembly of non-unitary bodies. At least the external surfaces of body 10 may be coated with a continuous layer of pyrolytic carbon to enhance biocompatability. This is particularly of importance for surfaces that will be blood contacting surfaces such as the bore when blood is at flow therethrough. Pyrolytic carbon coatings are known to be biologically compatible materials and have been used in implanted structures. See, for example, U.S. Pat. No. 3,783,868. Alternatively, the body 10 may be uncoated titanium or other rigid material. As illustrated in FIG. 7, a snugly fitting sleeve member 34 of graphite lines the interior of tube 12 and underlies coating 13. For coating the interior of a tube, it has been found desirable to have the graphite sleeve to serve as a substrate for the pyrolytic carbon.

Expanded polytetrafluoroethylene tubes 14 are shown joined to ends of 12 by slipping over these ends. Dacron (polyethyleneterephthalates) or other body compatible polymeric materials may be used rather than polytetrafluorethylene. The expanded polytetrafluoroethylene slipped over the ends of 12 may be provided as an intermediary for joining blood vessels to the assembly 10. A Teflon shrink bank 67 aids in holding the sleeve on. A suitable expanded polytetrafluoroethylene is sold under the trade name Gore-Tex by W. L. Gore Company of Newark, Del. It should be understood that tubes 14 are elective in that it is not necessary that they be present.

Figure 12:
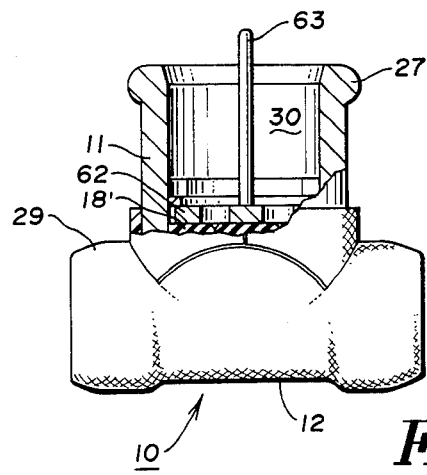
FIG. 12 is a side cut away view of the assembly of FIG. 11 where the coating with pyrolytic carbon is not included.

Alternatively, an uncoated device 10 as shown in FIG. 12 may be directly placed in a blood vessel. In such a case, the blood vessel would be slit longitudinally for a sufficient distance for the device 10 to be inserted and the vessel drawn around the device and sutured into place. A collar member 29, as described below, would be used around a portion of the stem to aid in tissue ingrowth to the stem portion.

As can best been seen in FIGS. 3 and 7, body 10 is formed with an internal extension 15 which substantially provides a separation of the internal chamber of T-shaped member 11 from the cavity of portion 12 except for the openings 16 and 17. Member 15 provides a support surface for a septum member 18. As can be seen in FIG. 3 the inner facing surface of member 18 is contiguous to the support 15 with the inner facing surface of member 18 substantially parallel to the interior bore of arms 12. Member 18 is formed of an elastomer such as natural rubber and as can be seen in FIGS. 2, 4, 5, and 6, has a broadly elliptical configuration. The purpose of this shape is best understood with reference to FIG. 2.

In FIG. 2, there is seen a top view of stem 11. As can be seen, stem 11 has a generally round opening. There is provided an internal shape in the opening along the axis of tube 12 which conforms generally to the ends 19 of the septum 18 for indexing purposes.

As can be seen in FIGS. 2, 4, 5, and 6, septum 18 is pre-cut in a three directional star or tricuspid form 20. Preferably, although not mandatorily the hole 21 may be completely through septum 18. These cuts facilitate passage of a needle through the septum. At the outer surface of the septum 18, there is a counter sunk region 36 for receiving a needle. The cuts 20 are positioned so that when member 18 is indexed into the opening of T-stem 11, cuts 20 are centered on openings 16 and 17. As a preferred alternative, the needle opening in septum 18 may be actually formed into the septum at the time the septum is fabricated. When the septum is pressed into place, the compression will seal the openings 21 (See FIGS. 11 and 12 also).

Overlying septum 18 is a pressure plate 22 of titanium or the like which defines openings 23 which are spaced to conform in position to slits 20 and openings 16 and 17. Pressure plate 22 is in turn locked into engagement with septum 18 by a spring retaining ring 24.

A cap member 26 snaps over a flanged edge 27, as seen in FIG. 8 and is held in sealed relationship therewith by a retaining ring 28. The lower flared edge 29 of cap 26 will be spaced, in use, slightly above the skin 25 of the user. Pressure contact with the skin of flange 27 is undesirable as necrosis may occur. Overall there is provided a profile for the exposed external portion of member 10 that is less likely to catch an object such as clothing. Cap 26 also provides a means whereby an antiseptic such as Betadine (iodine polyvinylpyrolidone complex) may be included in cavity 30 to maintain the unit sterile between usage.

The assembly described above is implantable in the patient by surgical techniques that are known and form no part of the invention. It is desirable to have the amount of the stem protruding above the skin line at a minimum amount compatible with permitting a cap member seal. Implantation may be in various manners and modes including but not limited to the following: by anastomosis to 14, ie by splicing the ends of a blood vessel to opposite ends of assembly 10. Assembly 10 may be positioned into a blood vessel that has been longitudinally slit for a distance sufficient to permit insertion of the device. In this latter case, the blood vessel is sutured about the device to form a seal and the sleeves 14 are not used.

To aid in accomplishing tissue growth onto the portion of the stem 11 below the skin line 25, a collar member 29 of porous plastic material such as polyethylene terephthalate, sold by E. I. Dupont under the trademark Dacron may be used. The portion of stem 11 above the dermis region is uncoated to reduce the risk of infection occurring by bacteria making their way down along the collar 29. If the external surface of stem 11 is titanium, the titanium may have a matte surface in the region of collar 29 and thus, eliminate need of collar 29.

When access is to be made to the blood system, the cap 26 is removed. The interior cavity region 30 thus exposed can be rinsed with appropriate sterilizing agents that are removed prior to insertion of a needle through openings 23, 20 and 16. It is preferred that cavity 30 be filled with and hold a sterilizing solution, such as described previously, between usage. This sterilizing solution can be placed in cavity 30 before closing with cap 26 or a hypodermic may be used to inject the solution through the cap. Desirably, the needle used to penetrate the septum will have a closed rounded end with an opening 34 at the side thereof. A blood sample can be drawn or material such as drugs inserted through the needle as desired.

The device described can be implanted into a patient and remain essentially permanently. However, if a need arises to replace the septum 18 after prolonged use, this can readily be done without need of surgical procedures. A modified forceps 31 is machined or ground to provide tips 32 of a size to be positioned into holes or recesses 33 in retaining ring 24. The ring may be withdrawn along with pressure plate 32 and septum 18 for cleaning and/or replacement. Of course, steps should be taken to block the body blood pressure so as to prevent appreciable blood flow outwardly through openings 16 and 17 during the assembly or disassembly.

To insure a tight seal of septum 18, with the interior wall of stem 11, it may be desirable to shape the side walls 35 of the septum in a concave manner as shown. A second purpose in such shaping is to provide for the displaced material of septum 18 resulting from introduction of needles through the septum.

While the implanted assembly 10 can be used with conventional hypodermic assemblies, it is desirable to utilize a cooperating assembly such as a member 40. Even when a simple needle is on a standard syringe, it is desirable that the needle have a rounded end as will be described below. Member 40 is constructed of a cylindrical block of metal 41 through which two hollow needle members 42 and 43 extend in sealed relationship to member 41. These needle members are positioned so as to index with openings 23 in pressure plate 22. As can best be seen in FIG. 7, the needles have rounded closed ends 44 and have a side opening 45 and 46 respectively. As shown, the needle is solid (cavityless) below the lower edge of openings 45 and 46. This construction is highly advantageous. The rounded closed end readily passes through septum 18 with a reduced tendency to cut and break pieces of a septum as a result of passage therethrough over use of a conventional hypodermic needle. The solid lower end avoids the presence of entrapped air. One can also position the openings in the needles so that if blood flow is in the direction shown by arrow 47, the needle opening 45 is directional to withdrawal of blood while opening 46 is directional to return of blood. The top of the needle can be joined to any suitable construction to be connectable to external blood flow tubing or other types of apparatus.

Figure 9:
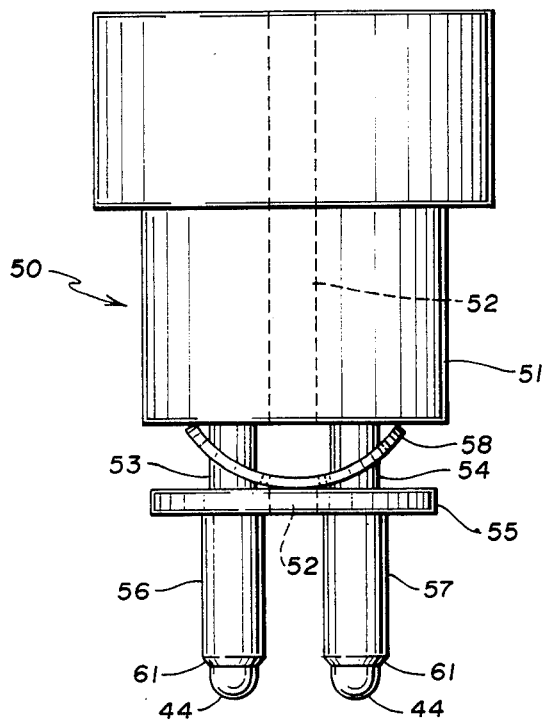
FIGS. 9 and 10 illustrate a needle and sheath assembly showing respectively the sheath covering the opening in the needle end and withdrawn to expose the opening.
Figure 10:
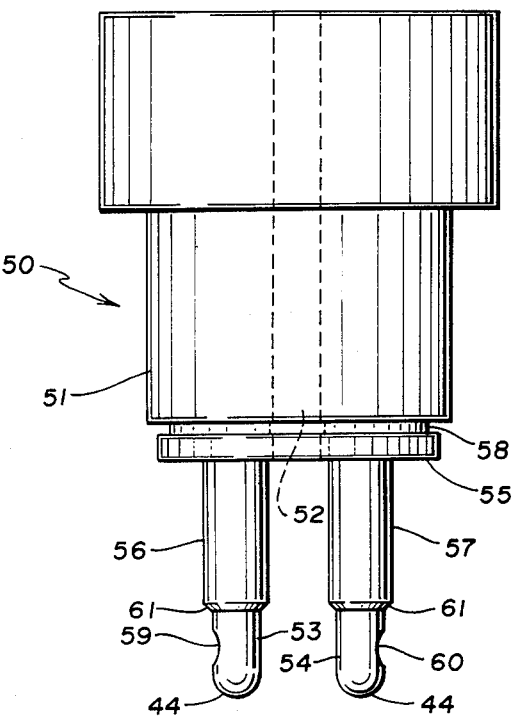

Referring now to FIGS. 9 and 10, there is illustrated a preferred form of needle assembly generally designated 50 for use with the implanted portion 10. In this preferred form, there is provided a block of plastic or metal 51 which is of a size to fit down into the cavity of stem 11 in a manner similar to that shown in FIG. 7. However, in this instance, member 51 includes an off center opening therethrough 52 for use as will be described below. Needle members 53 and 54 pass through member 51 and in conjunction with some type of tubing, syringe, or the like (not shown). The needle members are of a substantially identical configuration to that described with respect to FIG. 7. A sheath assembly 55 is provided having two rigid sleeve members 56 and 57 respectively, that are of a hollow configuration, such as a slip over needles 53 and 54 respectively. Members 56 and 57 are welded or otherwise secured to plate 55. In an uncompressed condition, the assembly 55 is held in position as seen in FIG. 9 by a spring member 58. In this position, the openings 59 and 60, as best seen in FIG. 10, are covered by sleeves 56 and 57. As can be seen in FIGS. 9 and 10, the sleeve members have a rounded shoulder 61 at the lower edge thereof which facilitates the penetration of the openings through septum 18. The length of sleeves 56 and 57 are sufficient to insure that the openings 59 and 60 do not act as a cutting edge to slice material of the septum off as the needles are penetrated through the septum. Once the sleeves have penetrated through the septum by assertion of the assembly into the top of stem 11, resistance of the pressure plate 22 and retaining ring 24 force spring 58 into a flat shape as illustrated in FIG. 10 and the sleeves 56 and 57 no longer cover openings 59 and 60.

Figure 11:
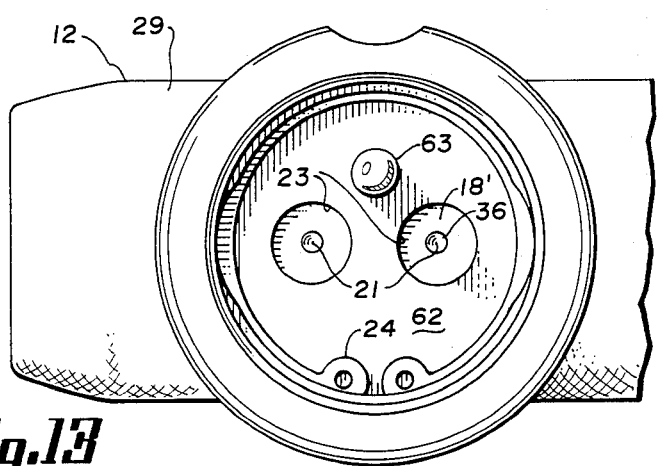
FIG. 11 is a top plant view of an assembly including a pressure plate with an aligning peg.
Figure 13:
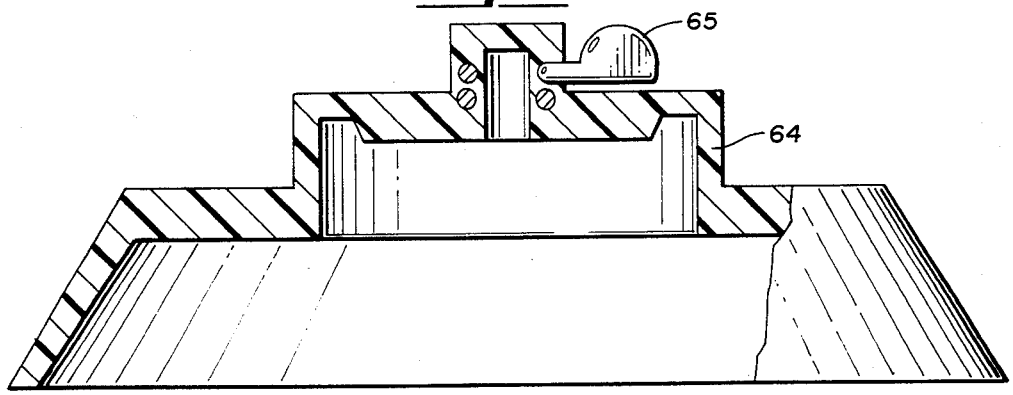
FIG. 13 is a side elevational view, partially cut away of a modified sealing cap.

With reference to FIGS. 11 and 12, it will be seen that the implanted portion of the device is substantially identical to what has been described previously with respect to the FIGS. 1 through 7 except for the absence of pyrolytic coating and other differences to be described. The differences lie in the usage of a pressure plate 62 which has projecting upwardly therefrom an off-center locater pin 63 which is positioned so as to cooperate with opening 52 of the needle assembly as illustrated in FIGS. 9 and 10. This locater pin provides two functions. First, when one is utilizing the needle assembly, it insures proper alignment of the needle members with the openings through the pressure plate and septum. Second, when the implanted device is not being used to gain access to the blood vessels, the pin 63 is utilized as a further attaching means to secure a cap 64 (see FIG. 13) to the exposed portion of stem 11. As can be best seen in FIG. 13, the cap member is adapted to slip over the edges of the stem portion member 10 to provide a sealing engagement therewith. In this instance, rather than having a retaining ring 28 completely surround the cap and stem portion, a built-in retaining ring 65 aids in gripping the locater stem 63 insuring that the cap is held in tight relationship with stem 11. As in the instance of the description with regard to FIG. 8, the cavity between the pressure plate 22 and the top of the stem 11 is again normally kept full of a sterilizing solution so as to insure that the device is ready for the next actual access use to the blood stream.

It will be noted in FIGS. 11 and 12 that the septum member 18' is shown as having a precast opening 21 therethrough described above. As the septum has been squeezed into place in the stem, the hole has been closed by the natural resiliency of septum 18 although it readily opens to accept needles.

I claim:
1. An implantable access device for providing access to the circulatory system comprising:
   a rigid body of biologically compatible material, said body having a generally T-shaped tubular configuration with the stem of the T joined to and in fluid communication with the arms of the T, support means internal to and at the junction of the stem and arms, a elastomeric septum member within the stem having first and second sides and positioned therein so that a portion of said first side is contiguous with and supported by said support means with the remaining portion of said first side that is exposed to the tube of said arms generally parallel with the upper inner surface of said arms, and septum retaining means within said stem member above said second side for compressively supporting said septum member therein in fixed relationship to said arms thereby sealing said stem opening when it is positioned within the cavity of said stem.

2. A device in accordance with claim 1 wherein said support means comprises a support member depending from and projecting inwardly into the cavity of said stem adjacent the inner tube surfaces of the arms, said support member constructed and arranged to support said first side of said septum member in fixed relationship to said arms and said septum retaining means comprises removable means compressively contacting said second side of said septum member.

3. An implantable blood access device in accordance with claims 1 or 2 wherein a porous biocompatible polymeric material surrounds at least the lower portion of the stem of the T.

4. An implantable blood access device in accordance with claim 3 wherein polymeric material is polyethylene terephthalate.

5. An implantable device in accordance with claim 1 wherein tubular sleeve members of a biocompatible polymeric material are in engagement with and extend from the remote ends of the arms to facilitate attachment of blood vessels to the arms.

6. An implantable device in accordance with claim 5 wherein said polymeric material is expanded polytetrafluorethylene.

7. An implantable device in accordance with claim 3 wherein tubular sleeve members of a biocompatible polymeric material are in engagement with and qxtend from the remote ends of the arms to facilitate attachment of blood vessels to the arms.

8. The device in accordance with claims 1 or 2 wherein at least the blood contacting surfaces of said body have a coating of a pyrolytic carbon.

9. A device in accordance with claim 1 wherein a tubular sleeve member of graphite is positioned within and in contact with the interior surface of said arms and a coating of pyrolytic carbon covers the surfaces of said device and said graphite sleeve that are in tissue and blood contact when in use.

10. The device in accordance with claim 1 wherein said elastomeric septum is provided with an opening extending at least partially through said septum to facilitate insertion of a hollow needle therethrough and said pressure plate has an opening therethrough in alignment with said septum opening.

11. The device in accordance with claim 1 wherein said stem member has a shoulder at the outer upper edge thereof and a sealing cap member releasably sealing the open end of said stem member, means holding said cap member to said stem, said cap member having a flared cone-shaped outer periphery that extends downwardly a distance so as to be adjacent the skin when said device is implanted.

12. A device in accordance with claim 2 wherein said support member extends across the opening in said stem, said support member defining at least one opening therethrough for receiving a needle.

13. A device in accordance with claim 1 wherein said septum member has a concave edge portion to facilitate sealing to the interior wall of said stem and provide for expansion of said septum when needle displaces material of the septum member.

14. A device in accordance with claim 10 wherein said septum member interior has at least a portion thereof noncircular and septum has a conforming shape so as to index the openings therethrough in a predetermined orientation.

15. A device in accordance with claim 2 wherein said septum has self-sealing openings at least partially through said septum positioned so as to be in assembled alignment with an opening in said support member.

16. In combination an implantable blood access device for providing access to blood and a needle assembly for linking said blood access device to an external apparatus wherein the blood access device comprises a rigid body of a biologically compatible material, said body having a generally T-shaped tubular configuration with the stem of the T joined to and in fluid communication with the arms of the T, an elastomeric septum member having first and second sides, means within said stem member supporting said septum member in fixed relationship to said arm members when it is positioned within and occupying a portion of the cavity of said stem, and wherein said needle assembly comprises a body member having a shape and size to be insertable at least partially within the tube cavity of said stem member, said body member having a tubular needle extending therethrough, said needle extending for a distance beyond said body member sufficient to penetrate through said septum member into the tube of said arms when in operative engagement with said stem member.

17. The combination in accordance with claim 16 wherein said needle has a rounded lower end and an opening to the internal region in the lower side of said needle.

18. The combination in accordance with claim 17 wherein said needle is solid below said side opening.

19. An implantable access device for providing access to the circulatory system comprising:

a rigid body of biologically compatible material, said body having a generally T-shaped tubular configuration with the stem of the T joined to and in fluid communication with the arms of the T, a support member depending from and projecting inwardly into the cavity of said stem adjacent the inner tube surfaces of the arms, an elastomeric septum member having first and second sides, said support member constructed and arranged to support said first side of said septum member in fixed relationship to said arms when the septum is positioned within the cavity of the stem, a pressure plate on said second side of said septum member in contacting relationship therewith and removable retaining means for locking said plate in contact with said septum.

20. A device in accordance with claim 1 wherein a portion of said stem above said septum second side defines an excutaneous cavity above the septum which is adapted to retain an antiseptic material.

21. A device in accordance with claim 1 wherein said septum member is constructed and arranged within said stem so as to permit lateral displacement of septum material when a needle penetrates the septum.

* * * * *